US006342035B1

(12) United States Patent
Kroll et al.

(10) Patent No.: US 6,342,035 B1
(45) Date of Patent: Jan. 29, 2002

(54) HEARING ASSISTANCE DEVICE SENSING OTOVIBRATORY OR OTOACOUSTIC EMISSIONS EVOKED BY MIDDLE EAR VIBRATIONS

(75) Inventors: Kai Kroll, Minneapolis; Scott C. Meyerson, Moundsview, both of MN (US)

(73) Assignee: St. Croix Medical, Inc., Minneapolis, MN (US)

( * ) Notice: Subject to any disclaimer, the term of this patent is extended or adjusted under 35 U.S.C. 154(b) by 0 days.

(21) Appl. No.: 09/499,076

(22) Filed: Feb. 4, 2000

Related U.S. Application Data

(60) Provisional application No. 60/118,582, filed on Feb. 5, 1999.

(51) Int. Cl.[7] .......................... H04R 25/00; A61N 1/08

(52) U.S. Cl. ........................................... 600/25; 607/57

(58) Field of Search ............................ 600/25; 607/137, 607/57, 56; 381/328, 68; 623/10

(56) References Cited

U.S. PATENT DOCUMENTS 5,776,179 A * 7/1998 Ren et al. .................. 607/137
5,879,283 A * 3/1999 Adams et al. ............... 600/25
5,954,628 A * 9/1999 Kennedy .................... 600/25
5,999,856 A * 12/1999 Kennedy .................... 607/57

* cited by examiner

*Primary Examiner*—Eric F. Winakur
*Assistant Examiner*—Nikita R Veniaminov
(74) *Attorney, Agent, or Firm*—Fredrikson & Byron, P.A.

(57) ABSTRACT

A total middle ear implantable (T-MEI) or partial middle ear implantable (PMEI) hearing assistance system provides a transient middle ear mechanical vibration stimulus, and senses emissions from the cochlea. The sensed cochlear emissions include mechanical vibrations ("otovibratory emissions") and sound pressure waves ("otoacoustic emissions"). Based on the sensed emissions, diagnostic information is provided to the physician at an external programmer, allowing easier positioning and coupling of an electrical-to-mechanical output transducer. Diagnosis of auditory system or hearing assistance system malfunctions is effectively implemented using the data communicated from the implantable hearing assistance device. Signal processing parameters are adjusted based on the sensed cochlear emissions for improved hearing assistance. Otovibratory emission sensing is likely more sensitive than otoacoustic emissions, providing improved audiometric screening data.

26 Claims, 9 Drawing Sheets

HEARING ASSISTANCE DEVICE SENSING OTOVIBRATORY OR OTOACOUSTIC EMISSIONS EVOKED BY MIDDLE EAR VIBRATIONS

CROSS REFERENCE TO RELATED APPLICATIONS

This application claims benefit of Provisional Appln. 60/118,582 filed Feb. 5, 1999.

This application is related to co-pending, commonly assigned U.S. patent application entitled IMPLANTABLE HEARING SYSTEM HAVING MULTIPLE TRANSDUCERS, Ser. No. 08/693,430, filed on Aug. 7, 1996, and assigned to the assignee of the present application, and which is herein incorporated by reference. This application is also related to a co-pending, commonly assigned U.S. patent application entitled IMPLANTABLE HEARIG ASSISTANCE SYSTEM WITH CALIBRATION AND AUDITORY RESPONSE TESTING, Ser. No. 08/804,016, filed on Feb. 21, 1997, and assigned to the assignee of the present application, and which is herein incorporated by reference.

BACKGROUND OF INVENTION

1. Field of the Invention

This invention relates generally to auditory diagnosis and assistance and more particularly, but not by way of limitation, to an at least partially implantable hearing assistance system providing middle ear vibrations and sensing particularly based on evoked otovibratory and otoacoustic emissions.

2. Description of Related Art

Some types of partial middle ear implantable (P-MEI), total middle ear implantable (T-MEI), cochlear implant, or other hearing assistance systems utilize devices disposed within the middle ear or inner ear regions. Such devices might include an input transducer for receiving sound vibrations or an output stimulator for providing mechanical or electrical output stimuli corresponding to the received sound vibrations.

An example of such a device is disclosed in U.S. Pat. No. 4,729,366, issued to D. W. Schaefer on Mar. 8, 1988. In the ’366 patent, a mechanical-to-electrical piezoelectric input transducer is associated with the malleus, transducing mechanical energy into an electrical signal, which is amplified and further processed by an electronics unit. A resulting electrical signal is provided to an electrical-to-mechanical piezoelectric output transducer that generates a mechanical vibration coupled to an element of the ossicular chain or to the oval window or round window for assisting hearing. In the ’366 patent, the ossicular chain is interrupted by removal of the incus. Removal of the incus prevents the mechanical vibrations delivered by the piezoelectric output transducer from mechanically feeding back to the piezoelectric input transducer.

Introducing devices into the middle or inner ear regions typically involves intricate surgical procedures for positioning or affixing the devices and its components for communication or coupling to the desired auditory elements. The proper positioning and affixation for obtaining the best input signal and providing the best output stimuli is a often a difficult task. The patient is typically under general anesthesia, and is thus unable to provide the implanting physician with any human feedback or information regarding how well sound is being perceived. Thus, the implanting surgeon faces a difficult task that may yield uneven results in the proper positioning and affixation of components in the middle or inner ear regions in order to obtain proper sound perception. There is a need in the art to facilitate optimal positioning and affixing components in the middle or inner ear regions in order to obtain proper sound perception. After implantation, the physician would like to diagnose malfunctions of the hearing assistance system without performing further invasive procedures. It is possible for an implanted device or component to become dissociated from its corresponding auditory element (e.g., by a severe blow to the head or otherwise). Further, changes in one or more of the ossicular chain elements may result in the displacement and misalignment of the device or its components. For example, an output transducer initially positioned to be in contact with the stapes may later become dissociated from the stapes. There is, therefore, a need in the art to enable a physician to determine, without surgical intervention, whether or not the output transducer or other implanted component is still properly positioned.

Other complicating factors are also present. There may be a large variation between patients in the sound perception characteristics of their auditory systems. Moreover, there may be variations between hearing assistance systems, such as in their component characteristics. For example, the characteristics of the input transducer and output stimulator may well vary to some degree. Accordingly, there is a need for hearing assistance systems to provide diagnostic or calibration information to the physician, such as during or after the surgical implantation procedure, in order to ascertain efficacy and adjust therapy accordingly. There is a further need for self-calibration of such hearing assistance systems to increase their ease of use.

In the unrelated technological field of audiometric screening and diagnosis, numerous audiometric screening techniques have been developed to assess the state of a patient’s auditory system. Some of these techniques are designed to provide diagnostic information without active participation by the patient. Such techniques are particularly useful for sleeping, anesthetized, unconscious patients or newborn infants who lack the cognitive ability to provide feedback to the physician. One such technique involves detection of transient evoked otoacoustic emissions, also referred to as Kemp echoes, cochlear echoes, and delayed evoked otoacoustic emissions.

In order to perform clinical diagnosis using otoacoustic emissions, a brief acoustic (i.e., sound pressure wave) stimulus is provided by an earphone that is introduced into the external auditory canal. Evoked otoacoustic emissions are sounds generated within the normal inner ear (cochlea) in response to the acoustic stimulus after a 5–20 millisecond latency period. Resulting sound pressure waves corresponding to the evoked otacoustic emissions are detected by a microphone introduced into the external auditory canal. Responses to several stimuli are averaged, amplified, and filtered. Transient evoked otoacoustic emissions are measurable in normal-hearing persons. However, if hearing loss exceeds 40–50 dB, an otoacoustic emission typically cannot be evoked in response to a transient stimulus. As a result, the presence or absence of transient evoked otoacoustic emissions can be used as an audiometric screening tool.

However, using transient evoked otoacoustic emission as a clinical diagnostic tool presents numerous difficulties. One such problem results from spontaneous otoacoustic emissions, which are internal sounds emitted by the human ear even in the absence of an external stimulus. The presence of such spontaneous otoacoustic emissions can make the transient evoked otoacoustic emissions more difficult to detect. Another problem is presence of noise in the introduced acoustic stimulus and the detected acoustic response. Such noise includes electronic noise (e.g., from the microphone, preamplifiers, receiver, filters, etc.), body noise (including spontaneous otoacoustic emissions), and environmental acoustic noise that enters the external auditory canal. This type of noise sources tend to mask the evoked otoacoustic emission, making it more difficult to detect. Thus, there is a need in the art to improve the sensitivity of detecting transient evoked otoacoustic emissions. For the reasons stated above, and for other reasons stated below which will become apparent to those skilled in the art upon reading and understanding the present specification, there is a need for calibration and diagnostic capability of PMEI, T-MEI or other hearing assistance systems, and there is a need in the unrelated technological field of audiometric screening and diagnosis for improved techniques of detecting cochlear emissions such as transient evoked otoacoustic emissions.

SUMMARY OF THE INVENTION

The present invention provides techniques for detecting cochlear emissions and performing audiometric, calibration, and diagnostic functions in an at least-partially implantable hearing assistance system. The present invention facilitates the optimal orientation, positioning and affixing of hearing assistance system devices and components in the middle or inner ear regions to ensure proper sound perception. According to one aspect of the present invention, a physician can determine, without surgical intervention, whether or not an already-implanted component is still properly positioned. Another advantage of the present invention allows improved sensitivity detection of cochlear emissions.

In one embodiment, the invention provides a transducer adapted for sensing mechanical vibrations produced by an inner ear. In another embodiment, the invention provides an apparatus comprising an output transducer and a first input transducer. The output transducer is adapted for coupling a mechanical vibration output stimulus to an inner ear in response to an electrical output signal. The first input transducer is adapted for receiving an emission (e.g., transient evoked otovibratory or otoacoustic emission) from the inner ear and generating an electrical first input signal in response to the emission. The output and first input transducers can be integrally or separately formed.

In one embodiment, the apparatus includes an electronics unit that is capable of adjusting the electrical output signal based on the received electrical first input signal. In another embodiment, the apparatus includes a second input transducer. In yet another embodiment, the apparatus further comprises an external transceiver, adapted for communication with the electronics unit.

Another aspect of the invention provides a method that includes disposing a transducer in the middle ear, stimulating the inner ear using the transducer disposed in the middle ear, and sensing emissions (e.g., transient evoked otovibratory or otoacoustic emissions) from the inner ear in response to stimulating the inner ear.

In one embodiment, the method also includes programming a hearing assistance device based on the sensed emissions from the inner ear. Another embodiment includes adjusting the stimulation of the inner ear based on the sensed emissions from the inner ear. In yet another embodiment, a data signal, based on the sensed emissions from the inner ear, is stored, or communicated from an implanted transmitter to an external receiver. A further embodiment includes repositioning the transducer (or adjusting a contact force between the transducer and an auditory element) based on the sensed emissions from the inner ear. The invention also allows programming of hearing assistance signal processing parameters of an implantable hearing assistance device based on the sensed emissions from the inner ear.

Another aspect of the invention provides a method that includes stimulating the inner ear, sensing emissions from the inner ear in response to stimulating the inner ear, and programming an implantable device (e.g., adjusting a gain or frequency response) based on the sensed emissions from the inner ear.

As described below, the present invention allows improved sensitivity detection of cochlear emissions, and provides easier implantation and subsequent calibration, diagnostic, and audiometric functions of an implantable hearing assistance device.

BRIEF DESCRIPTION OF THE DRAWINGS

In the drawings, like numerals describe substantially similar components throughout the several views.

DETAILED DESCRIPTION OF THE INVENTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description is, therefore, not to be taken in a limiting sense, and the scope of the present invention is defined by the appended claims and their equivalents. In the accompanying drawings, like numerals describe substantially similar components throughout the several views.

As described below, the present invention provides improved techniques for detecting transient evoked otoacoustic emissions by providing a mechanical vibration in the middle ear, rather than providing an external acoustic (sound pressure) stimulus. The present invention detects resulting transient evoked otovibratory or otoacoustic emissions, in response to the mechanical vibration stimulus.

Sensing the resulting transient evoked otoacoustic emission includes either directly sensing a mechanical sound vibration (defined herein as an "otovibratory emission"), or sensing a resulting sound pressure wave (defined herein as an otoacoustic emission"). In one embodiment, detection of otovibratory and otoacoustic emissions provides calibration and diagnostic functions for a middle ear implantable hearing system such as a partial middle ear implantable (P-MEI), total middle ear implantable (T-MEI), or other hearing system. A P-MEI or T-MEI hearing system assists the human auditory system in converting acoustic energy contained within sound waves into electrochemical signals delivered to the brain and interpreted as sound.

Figure 1:
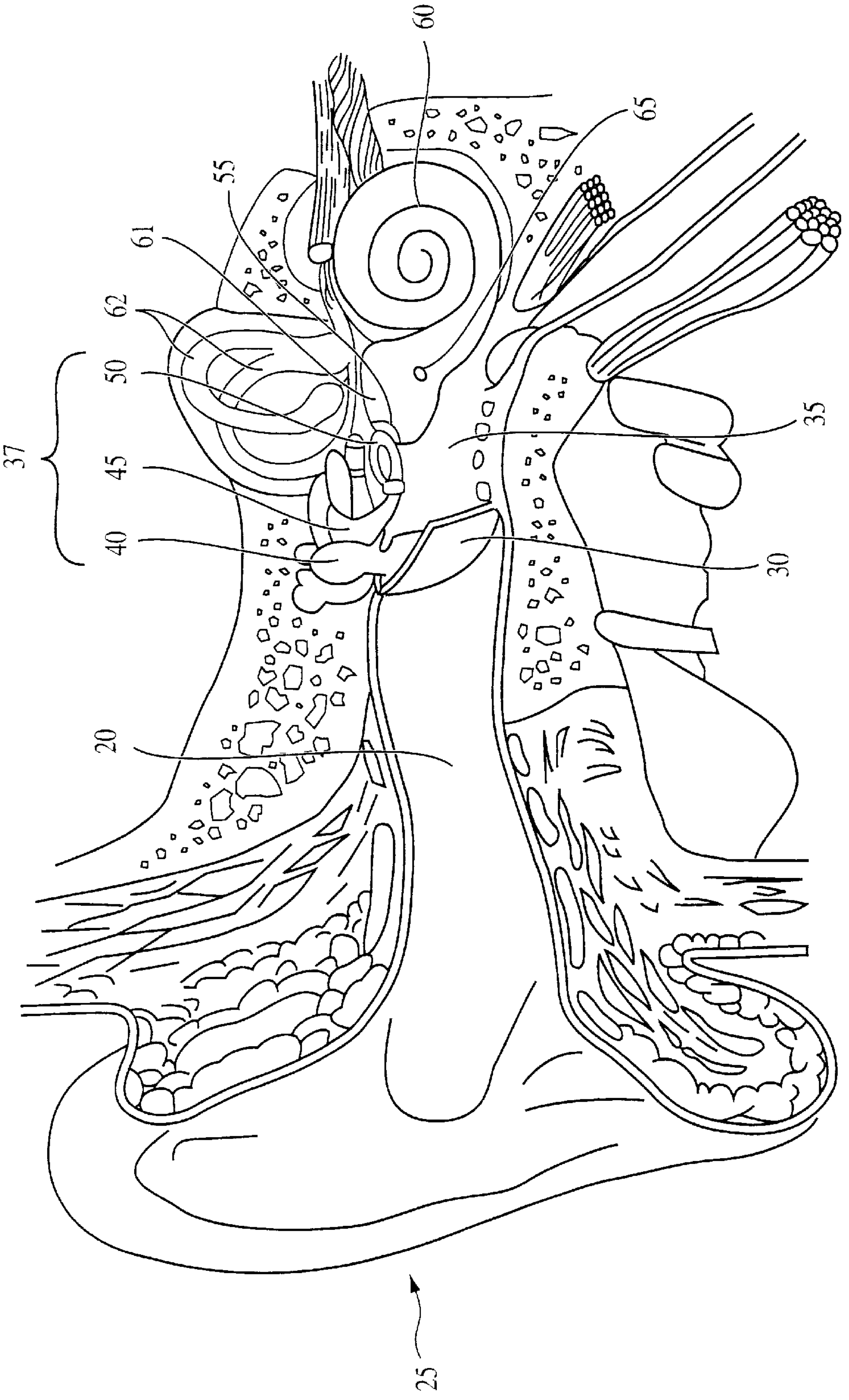
FIG. 1 illustrates generally a human auditory system.

FIG. 1 illustrates generally a human auditory system. Sound waves are directed into an external auditory canal 20 by an outer ear (pinna) 25. The frequency characteristics of the sound waves are slightly modified by the resonant characteristics of the external auditory canal 20. These sound waves impinge upon the tympanic membrane (eardrum) 30, interposed at the terminus of the external auditory canal 20, between it and the tympanic cavity (middle ear) 35. Variations in the sound waves produce tympanic vibrations. The mechanical energy of the tympanic vibrations is communicated to the inner ear, comprising cochlea 60, vestibule 61, and semicircular canals 62, by a sequence of articulating bones located in the middle ear 35. This sequence of articulating bones is referred to generally as the ossicular chain 37. Thus, the tympanic membrane 30 and ossicular chain 37 transform acoustic energy in the external auditory canal 20 to mechanical energy at the cochlea 60.

The ossicular chain 37 includes three ossicles: a malleus 40, an incus 45, and a stapes 50. The malleus 40 includes manubrium and head portions. The manubrium of the malleus 40 attaches to the tympanic membrane 30. The head of the malleus 40 articulates with one end of the incus 45. The incus 45 normally couples mechanical energy from the vibrating malleus 40 to the stapes 50. The stapes 50 includes a capitulum portion, comprising a head and a neck, connected to a footplate portion by means of a support crus comprising two crura. The stapes 50 is disposed in and against a membrane-covered opening on the cochlea 60. This membrane-covered opening between the cochlea 60 and middle ear 35 is referred to as the oval window 55. Oval window 55 is considered part of cochlea 60 in this patent application. The incus 45 articulates the capitulum of the stapes 50 to complete the mechanical transmission path.

Normally, prior to implantation of the invention, tympanic vibrations are mechanically conducted through the malleus 40, incus 45, and stapes 50, to the oval window 55. Vibrations at the oval window 55 are conducted into the fluid-filled cochlea 60. These mechanical vibrations generate fluidic motion, thereby transmitting hydraulic energy within the cochlea 60. Pressures generated in the cochlea 60 by fluidic motion are accommodated by a second membrane-covered opening on the cochlea 60. This second membrane-covered opening between the cochlea 60 and middle ear 35 is referred to as the round window 65. Round window 65 is considered part of cochlea 60 in this patent application. Receptor cells in the cochlea 60 translate the fluidic motion into neural impulses which are transmitted to the brain and perceived as sound. However, various disorders of the tympanic membrane 30, ossicular chain 37, and/or cochlea 60 can disrupt or impair normal hearing.

Hearing loss due to damage in the cochlea 60 is referred to as sensorineural hearing loss. Hearing loss due to an inability to conduct mechanical vibrations through the middle ear 35 is referred to as conductive hearing loss. Some patients have an ossicular chain 37 lacking sufficient resiliency to transmit mechanical vibrations between the tympanic membrane 30 and the oval window 55. As a result, fluidic motion in the cochlea 60 is attenuated. Thus, receptor cells in the cochlea 60 do not receive adequate mechanical stimulation. Damaged elements of ossicular chain 37 may also interrupt transmission of mechanical vibrations between the tympanic membrane 30 and the oval window 55.

Various techniques have been developed to remedy hearing loss resulting from conductive or sensorineural hearing disorder. For example, tympanoplasty is used to surgically reconstruct the tympanic membrane 30 and establish ossicular continuity from the tympanic membrane 30 to the oval window 55. Various passive mechanical prostheses and implantation techniques have been developed in connection with reconstructive surgery of the middle ear 35 for patients with damaged elements of ossicular chain 37. Two basic forms of prosthesis are available: total ossicular replacement prostheses (TORP), which is connected between the tympanic membrane 30 and the oval window 55; and partial ossicular replacement prostheses (PORP), which is positioned between the tympanic membrane 30 and the stapes 50.

Various types of hearing aids have been developed to compensate for hearing disorders. A conventional "air conduction" hearing aid is sometimes used to overcome hearing loss due to sensorineural cochlear damage or mild conductive impediments to the ossicular chain 37. Conventional hearing aids utilize a microphone, which transduces sound into an electrical signal. Amplification circuitry amplifies the electrical signal. A speaker transduces the amplified electrical signal into acoustic energy transmitted to the tympanic membrane 30. However, some of the transmitted acoustic energy is typically detected by the microphone, resulting in a feedback signal which degrades sound quality. Conventional hearing aids also often suffer from a significant amount of signal distortion.

Implantable hearing systems have also been developed, utilizing various approaches to compensate for hearing disorders. For example, cochlear implant techniques implement an inner ear hearing system. Cochlear implants electrically stimulate auditory nerve fibers within the cochlea 60. A typical cochlear implant system includes an external microphone, an external signal processor, and an external transmitter, as well as an implanted receiver and an implanted single channel or multichannel probe. A single channel probe has one electrode. A multichannel probe has an array of several electrodes. In the more advanced multichannel cochlear implant, a signal processor converts speech signals transduced by the microphone into a series of sequential electrical pulses corresponding to different frequency bands within a speech frequency spectrum. Electrical pulses corresponding to low frequency sounds are delivered to electrodes that are more apical in the cochlea 60. Electrical pulses corresponding to high frequency sounds are delivered to electrodes that are more basal in the cochlea 60.

The nerve fibers stimulated by the electrodes of the cochlear implant probe transmit neural impulses to the brain, where these neural impulses are interpreted as sound.

Other inner ear hearing systems have been developed to aid patients without an intact tympanic membrane 30, upon which "air conduction" hearing aids depend. For example, temporal bone conduction hearing systems produce mechanical vibrations that are coupled to the cochlea 60 via a temporal bone in the skull. In such temporal bone conduction hearing systems, a vibrating element can be implemented percutaneously or subcutaneously.

A particularly interesting class of hearing systems includes those which are configured for disposition principally within the middle ear 35 space. In middle ear implantable (MEI) hearing assistance systems, an electrical-to-mechanical output transducer couples mechanical vibrations to the ossicular chain 37, which is optionally interrupted to allow coupling of the mechanical vibrations thereto. Both electromagnetic and piezoelectric output transducers have been used to effect the mechanical vibrations upon the ossicular chain 37.

One example of a partial middle ear implantable (P-MEI) hearing system having an electromagnetic output transducer comprises: an external microphone transducing sound into electrical signals; external amplification and modulation circuitry; and an external radio frequency (RF) transmitter for transdermal RF communication of an electrical signal. An implanted receiver detects and rectifies the transmitted signal, driving an implanted coil in constant current mode. A resulting magnetic field from the implanted drive coil vibrates an implanted magnet that is permanently affixed only to the incus 45. Such electromagnetic output transducers have relatively high power consumption requiring larger batteries, which limits their usefulness in total middle ear implantable (T-MEI) hearing systems.

A piezoelectric output transducer is also capable of effecting mechanical vibrations to the ossicular chain 37. An example of such a device is disclosed in U.S. Pat. No. 4,729,366, issued to D. W. Schaefer on Mar. 8, 1988. In the '366 patent, a mechanical-to-electrical piezoelectric input transducer is associated with the malleus 40, transducing mechanical energy into an electrical signal, which is amplified and further processed by an electronics unit. A resulting electrical signal is provided to an electrical-to-mechanical piezoelectric output transducer that generates a mechanical vibration coupled to an element of the ossicular chain 37 or to the oval window 55 or round window 65. In the '366 patent, the ossicular chain 37 is interrupted by removal of the incus 45. Removal of the incus 45 prevents the mechanical vibrations delivered by the piezoelectric output transducer from mechanically feeding back to the piezoelectric input transducer.

The present invention provides improved techniques for detecting transient evoked otovibratory and otoacoustic cochlear emissions emitted in response to a mechanical sound vibration stimulus, rather than in response to a conventionally introduced sound pressure wave stimulus. In this patent application, the terms cochlea 60 and inner ear 60 are used interchangeably. The term otovibratory emission is defined as a mechanical sound vibration emitted from the cochlea 60. The term otoacoustic emission is defined as sound pressure wave (not a mechanical vibration) in a gaseous medium (e.g., air) emitted from the cochlea 60. According to conventional techniques, otoacoustic emissions are sensed via a microphone placed in the external auditory canal 20, and the otoacoustic emissions are generated by an acoustic (sound pressure wave) stimulus. According to one aspect of the present invention, a transient vibrational stimulus is used to evoke cochlear emissions. The transient vibrational stimulus may result in both transient evoked otovibratory and otoacoustic emissions.

Figure 2:
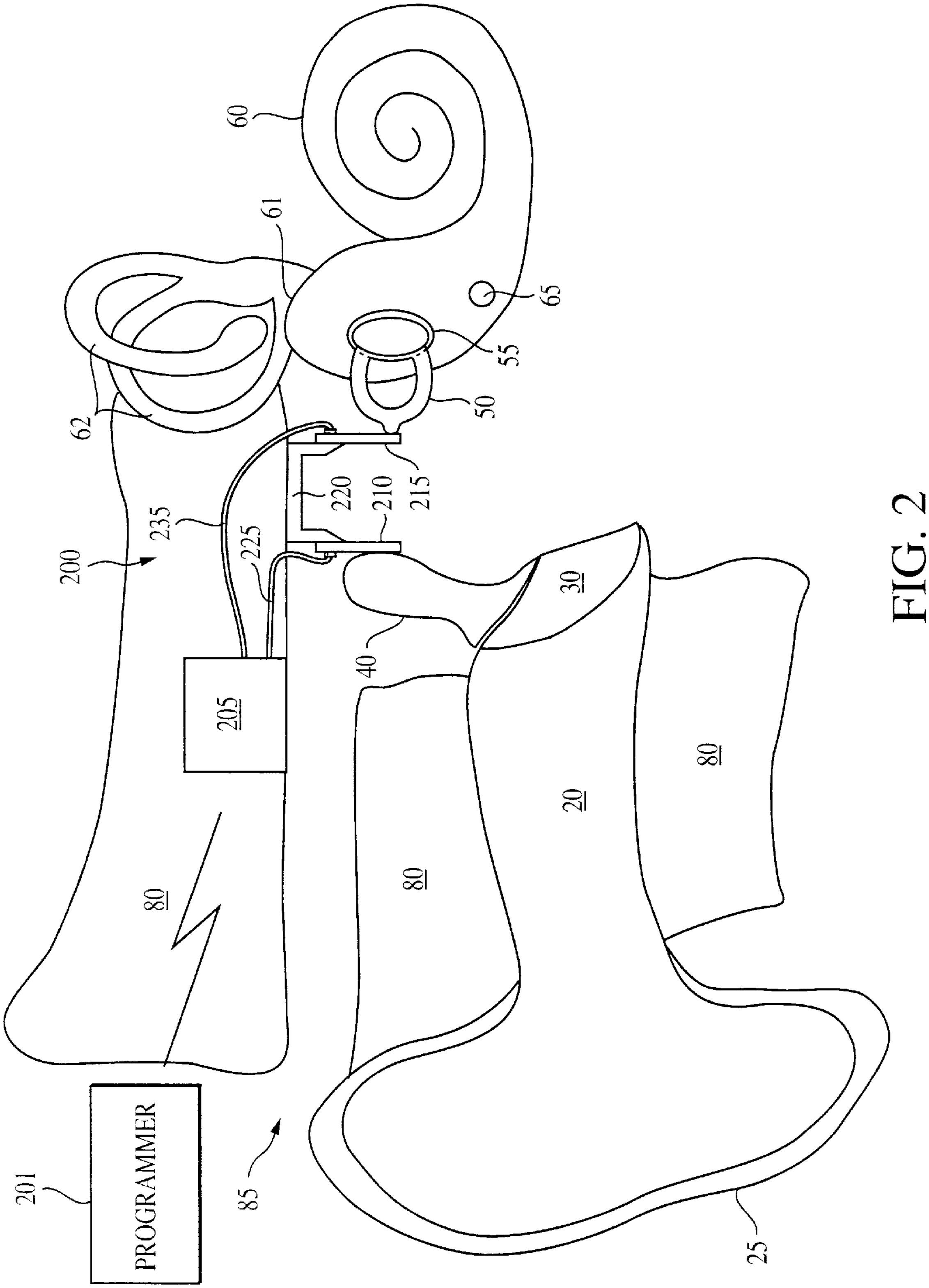
FIG. 2 is a schematic/block diagram illustrating generally a hearing assistance system according to one embodiment of the present invention.

FIG. 2 is a schematic/block diagram illustrating generally one embodiment of a hearing assistance system according to one embodiment of the present invention. This embodiment, by way of example, but not by way of limitation, includes total middle ear implantable (T-MEI) hearing assistance device 200 implanted in middle ear 35. Portions of hearing assistance device 200 are optionally implanted in the mastoid 80 portion of the temporal bone. In this embodiment, incus 45 is removed. However, such removal of incus 45 is not required to practice the invention. This embodiment of hearing assistance device 200 includes electronics unit 205, an input transducer 210, and an integrally formed input/output transducer 215. A carrier 220 is provided, such as for mounting portions of input transducer 210 and input/output transducer 215. Though a unitary carrier 220 is shown, input transducer 210 and input/output transducer 215 are also affixable by separate carriers or by any other suitable technique.

The hearing assistance system also includes an external (i.e., not implanted) programmer 201, which is communicatively coupled to an external or implantable portion of hearing assistance device 200, such as electronics unit 205. Programmer 201 includes hand-held, desktop, or a combination of hand-held and desktop embodiments, for use by a physician or the patient in which hearing assistance device 200 is implanted.

In one embodiment, each of programmer 201 and hearing assistance device 200 include an inductive element, such as a coil, for inductively-coupled bidirectional transdermal communication between programmer 201 and hearing assistance device 200. Inductive coupling is just one way to communicatively couple programmer 201 and hearing assistance device 200. Any other suitable technique of communicatively coupling programmer 201 and hearing assistance device 200 may also be used. In one embodiment, such communication includes programming of hearing assistance device 200 by programmer 201 for adjusting hearing assistance parameters in hearing assistance device 200, and also provides data transmission from hearing assistance device 200 to programmer 201, such as for parameter verification or diagnostic purposes. Programmable parameters include, but are not limited to: on/off, standby mode, type of noise filtering for a particular sound environment, frequency response, volume, delivery of a test stimulus on command, and any other adjustable parameter.

In a hearing assistance mode of operation, input transducer 210 senses the mechanical sound vibrations of an auditory element. In one embodiment, these mechanical sound vibrations are the result of external environmental sound pressure waves received in the external auditory canal 20, and converted into mechanical vibrations by the tympanic membrane 30. Input transducer 210 provides a resulting electrical input signal in response to the received mechanical sound vibrations of the auditory element. In the embodiment of FIG. 2, malleus 40 is illustrated, by way of example, as the auditory element from which vibrations are sensed, but other auditory elements are also capable of providing sound vibrations, including, but not limited to tympanic membrane 30, incus 45 or other ossicle, or any prosthetic auditory element serving a similar function.

Input transducer 210 provides the resulting electrical input signal, such as through one or more lead wires at node 225, to electronics unit 205. Electronics unit 205 provides amplification, filtering, or other signal processing of the input signal, and provides a resulting electrical output signal, such as through one or more lead wires, illustrated generally by node 235, to input/output transducer 215. In this embodiment, by way of example, but not by way of limitation, input/output transducer 215 provides mechanical (e.g., vibratory) stimulation to oval window 55 of cochlea 60 through stapes 50.

In one embodiment, input/output transducer 215 is also used to sense otovibratory emissions from cochlea 60 in response to an earlier-provided transient mechanical sound vibration stimulus. In this embodiment, input/output transducer 215 includes an integrally formed bidirectional transducer element (e.g., a piezoelectric element) for performing both electrical-to-mechanical and mechanical-to-electrical transduction. Input/output transducer 215 provides a vibrational stimulus to cochlea 60, and also senses an otovibratory emission from cochlea 60 in response to the vibrational stimulus. Input/output transducer 215 provides a resulting input electrical signal through a lead wire at node 235 to electronics unit 205. In another embodiment, input/output transducer 215 includes an electrical-to-mechanical transducer and a separately formed mechanical-to-electrical transducer, as described below.

Figure 3:
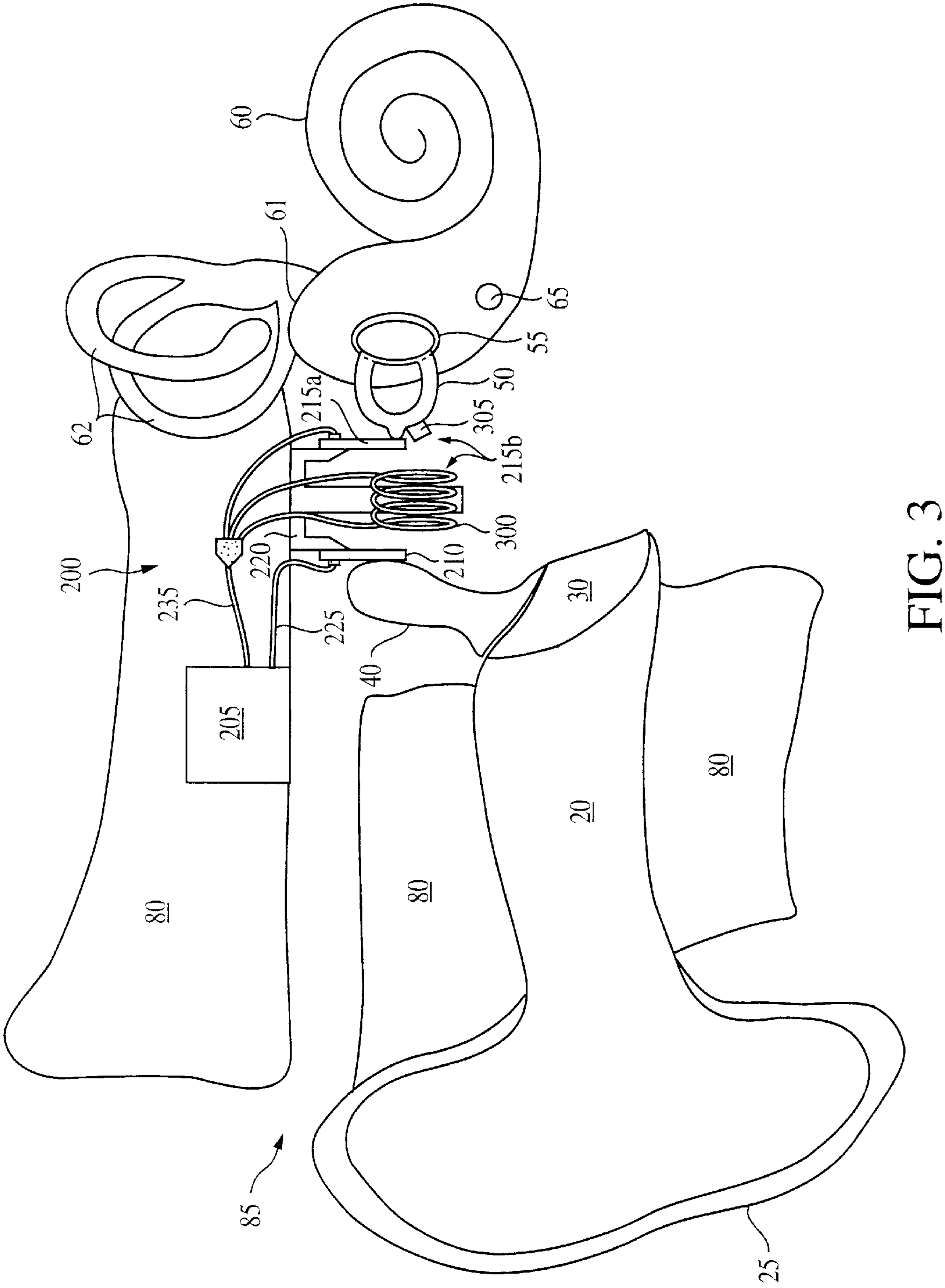
FIG. 3 is a schematic/block diagram illustrating generally a hearing assistance device according to another embodiment of the present invention.

FIG. 3 is a schematic/block diagram, similar to FIG. 2, illustrating generally a hearing assistance device 200 according to another embodiment of the present invention. However, in FIG. 3, input/output transducer 215 includes a separately formed input transducer element 215*a* and output transducer element 215*b*. By way of example, but not by way of limitation, input transducer element 215*a* includes a piezoelectric transducer element for sensing otovibratory emissions from cochlea 60, and output transducer element 215*b* includes an electromagnetic transducer comprising a coil 300 and permanent magnet 305 that is electromagnetically driven by coil 300. Output transducer element 215*b* provides mechanical vibrations to cochlea 60 both for assisting hearing and for stimulating evoked otovibratory and otoacoustic emissions.

Output element 215*b* is implemented as any type of electrical-to-mechanical transducer, including, but not limited to a piezoelectric transducer, electromagnetic transducer, or inductor type. Input transducer element 215*a* is implemented as any type of mechanical-to-electrical transducer, including, but not limited to a piezoelectric transducer, electromagnetic transducer, a capacitive transducer, an accelerometer and microphone (described below). Alternatively, input transducer element 215*a* is omitted, and otovibratory or otoacoustic emissions are sensed by input transducer 210, particularly when ossicular chain 37 is intact and functional. During a hearing assistance mode of operation, input transducer 210 senses mechanical vibrations resulting from environmental sounds, rather than from transient evoked otovibratory or otoacoustic emissions.

Figure 4:
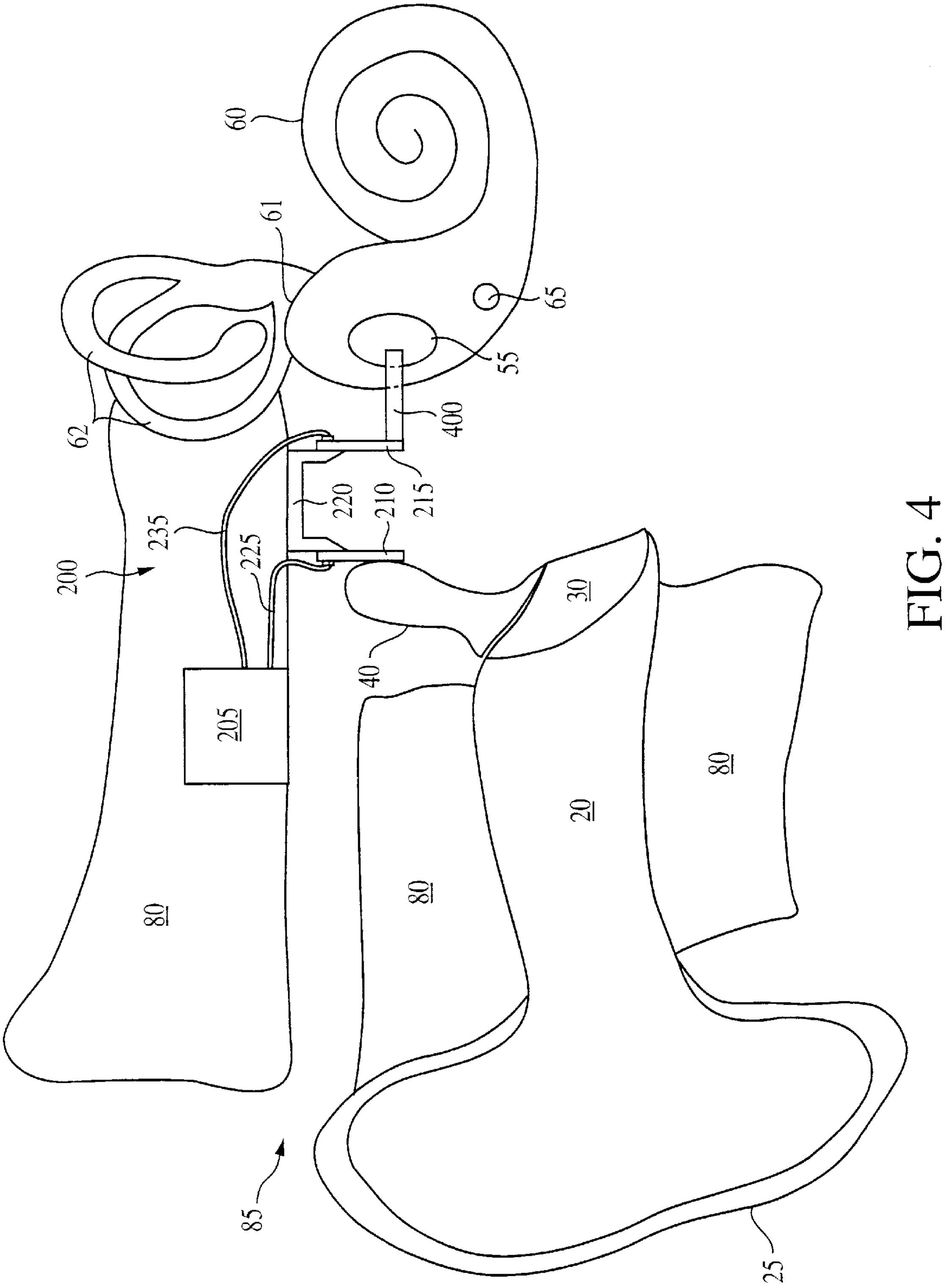
FIG. 4 is a schematic/block diagram illustrating generally a hearing assistance device according to a further embodiment of the present invention.

FIG. 4 is a schematic/block diagram illustrating generally a hearing assistance device 200 according to another embodiment of the present invention. In FIG. 4, stapes 50 is removed and input/output transducer 215 is mechanically coupled to cochlea 60 either directly, or via an intermediate coupling element 400. By way of example, but not by way of limitation, intermediate coupling element 400 can include a stiff rod or wire. Input/output transducer 215 provides mechanical vibrations to cochlea 60 both for assisting hearing and for stimulating evoked otovibratory or otoacoustic emissions. Input/output transducer element 215 also senses the resulting evoked otovibratory emissions from cochlea 60, providing a resulting electrical input signal through a lead wire at node 235 to electronics unit 225. Alternatively, otoacoustic emissions are sensed by microphonic input transducer 210, particularly when ossicular chain 37 is intact and functional. During a hearing assistance mode of operation, microphonic input transducer 210 senses environmental sounds, rather than transient evoked otoacoustic emissions.

Figure 5:
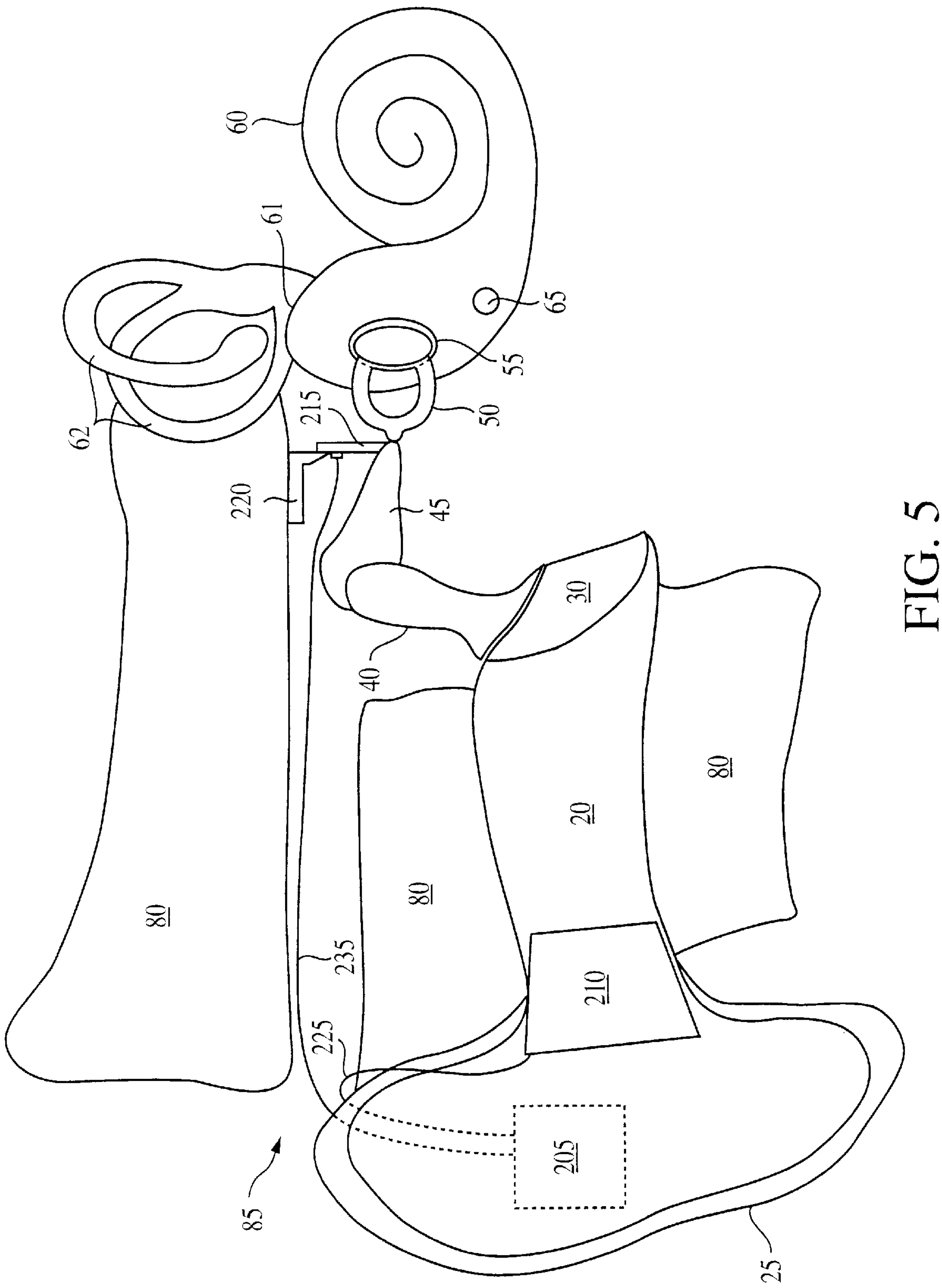
FIG. 5 is a schematic/block diagram illustrating generally a hearing assistance device according to a partial middle-ear implantable (P-MEI) embodiment of the present invention.

FIG. 5 is a schematic/block diagram, similar to FIG. 2, illustrating generally a hearing assistance device 200 according to a partial middle-ear implantable (P-MEI) embodiment of the present invention. FIG. 5 also illustrates, by way of example, but not by way of limitation, an embodiment in which incus 45 is present and ossicular chain 37 is intact. Also by way of example, but not by way of limitation in this embodiment, electronics unit 205 is not implanted, but is instead worn externally, such as behind pinna 25. Input transducer 210 includes an external microphone disposed in external auditory canal 20 or elsewhere, for transducing acoustic sound pressure waves into an electrical input signal. Input/output transducer 215 is mechanically coupled to incus 45, stapes 50, or directly to cochlea 60, as described above, providing mechanical vibrations for hearing assistance and stimulation of evoked otovibratory or otoacoustic emissions. In one embodiment, input/output transducer 215 also senses the resulting evoked otovibratory cochlear emissions. In another embodiment, input/output transducer 215 provides mechanical vibrations in middle ear 35 for stimulating resulting evoked otoacoustic emissions that are sensed by microphone 210 in external auditory canal 20. Alternatively, input/output transducer 215 is replaced by an output-only transducer (e.g., an electrical-to-mechanical transducer, as described above) for providing mechanical vibrations in middle ear 35 that stimulate resulting evoked otoacoustic emissions sensed by microphone 210 in external auditory canal 20.

Figure 6:
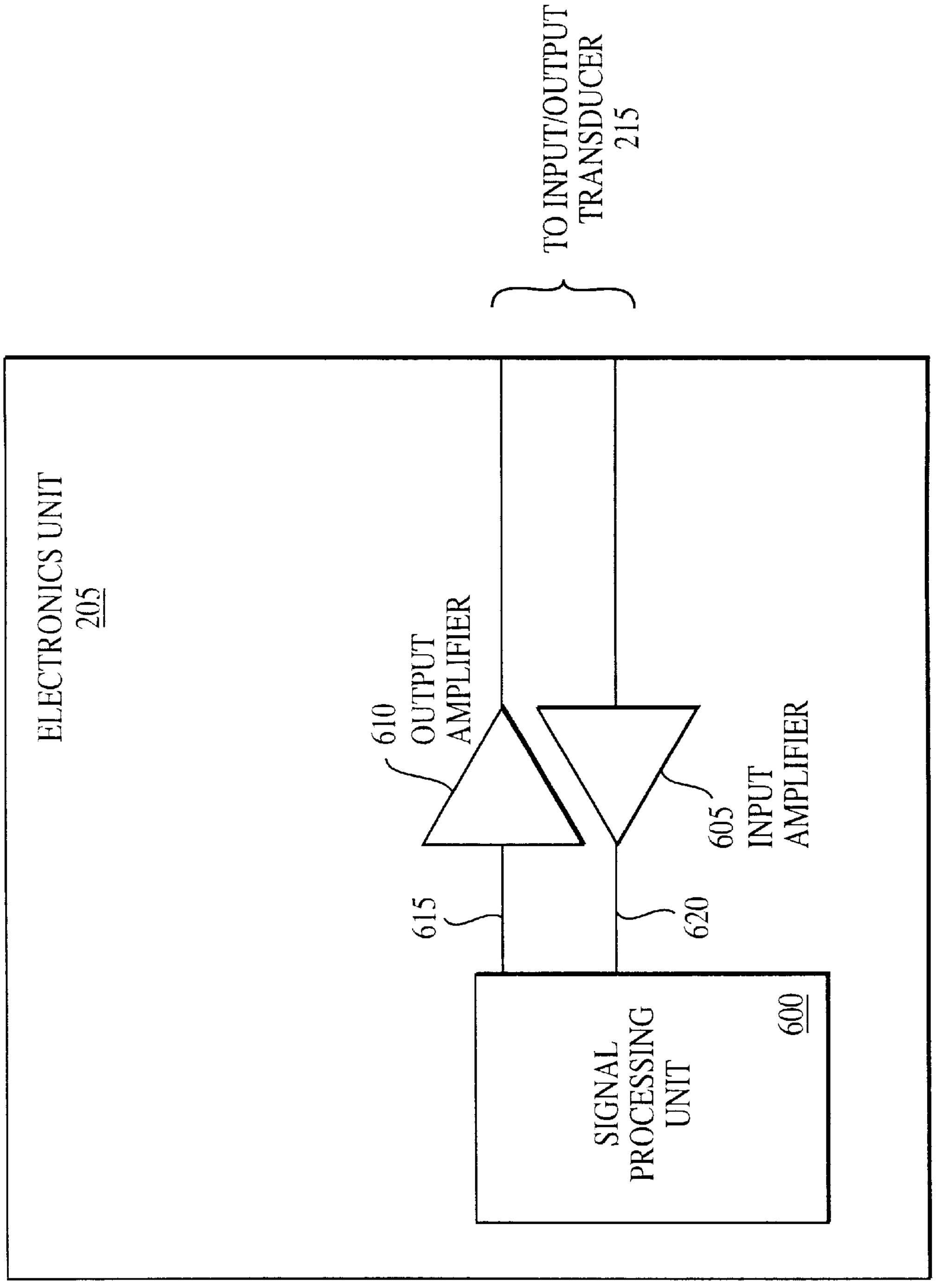
FIG. 6 is a schematic/block diagram illustrating generally one embodiment of at least a portion of an electronics unit according to one aspect of the present invention.

FIG. 6 is a schematic/block diagram illustrating generally one embodiment of at least a portion of electronics unit 205 according to one aspect of the present invention. In the embodiment of FIG. 6, electronics unit 205 includes a signal processing unit 600, an input amplifier 605, and an output amplifier 610. Input amplifier 605 and output amplifier 610 are each electrically coupled between signal processing unit 600 and input/output transducer 215 through one or more shared or separate lead wires illustrated generally by node 235 in FIGS. 2–5.

Output amplifier 610 receives an output electrical signal at node 615 from signal processing unit 600, and provides, in response thereto, a buffered or amplified electrical output signal for driving input/output transducer 215 and producing a mechanical vibration stimulus that is directly or indirectly coupled to cochlea 60. Input amplifier 605 receives an input electrical signal from input/output transducer 215 that is transduced from otovibratory or otoacoustic emissions from cochlea 60 that are evoked in response to an earlier-provided mechanical vibration stimulus thereto. In response to the input electrical signal received from input/output transducer 215, input amplifier 605 provides at node 620 a buffered or amplified input electrical signal to signal processing unit 600.

According to one aspect of the present invention, hearing assistance device 200 provides a middle ear 35 mechanical vibration stimulus to cochlea 60, rather than providing an external acoustic sound pressure wave stimulus. This is particularly advantageous when incus 45 is disarticulated (removed), or when sound pressure waves cannot be received by tympanic membrane 30 and transmitted as mechanical vibrations through ossicular chain 37 without interruption or attenuation.

According to another aspect of the present invention, hearing assistance device 200 is capable of efficient, high sensitivity detection of an evoked cochlear response. In this embodiment, otovibratory emissions are directly sensed, rather than indirectly sensing the resulting otoacoustic emission sound pressure waves in external auditory canal 20. Otovibratory emissions from cochlea 60 are likely communicated through ossicular chain 37, thereby driving tympanic membrane 30 to produce the otoacoustic emissions. The otoacoustic emissions are likely attenuated from the otovibratory emissions, and the otoacoustic emissions may be completely absent due to ossicular interruption or malfunction. Moreover, the frequency of otovibratory and otoacoustic emissions may differ. Otovibratory emissions likely allow more sensitive monitoring of cochlear response. The present invention allows the detection of both otovibratory and otoacoustic emissions from cochlea 60 to be used as a clinical audiometric diagnostic tool, or to be used in providing calibration and diagnostic functions in hearing assistance device 200.

Figure 7:
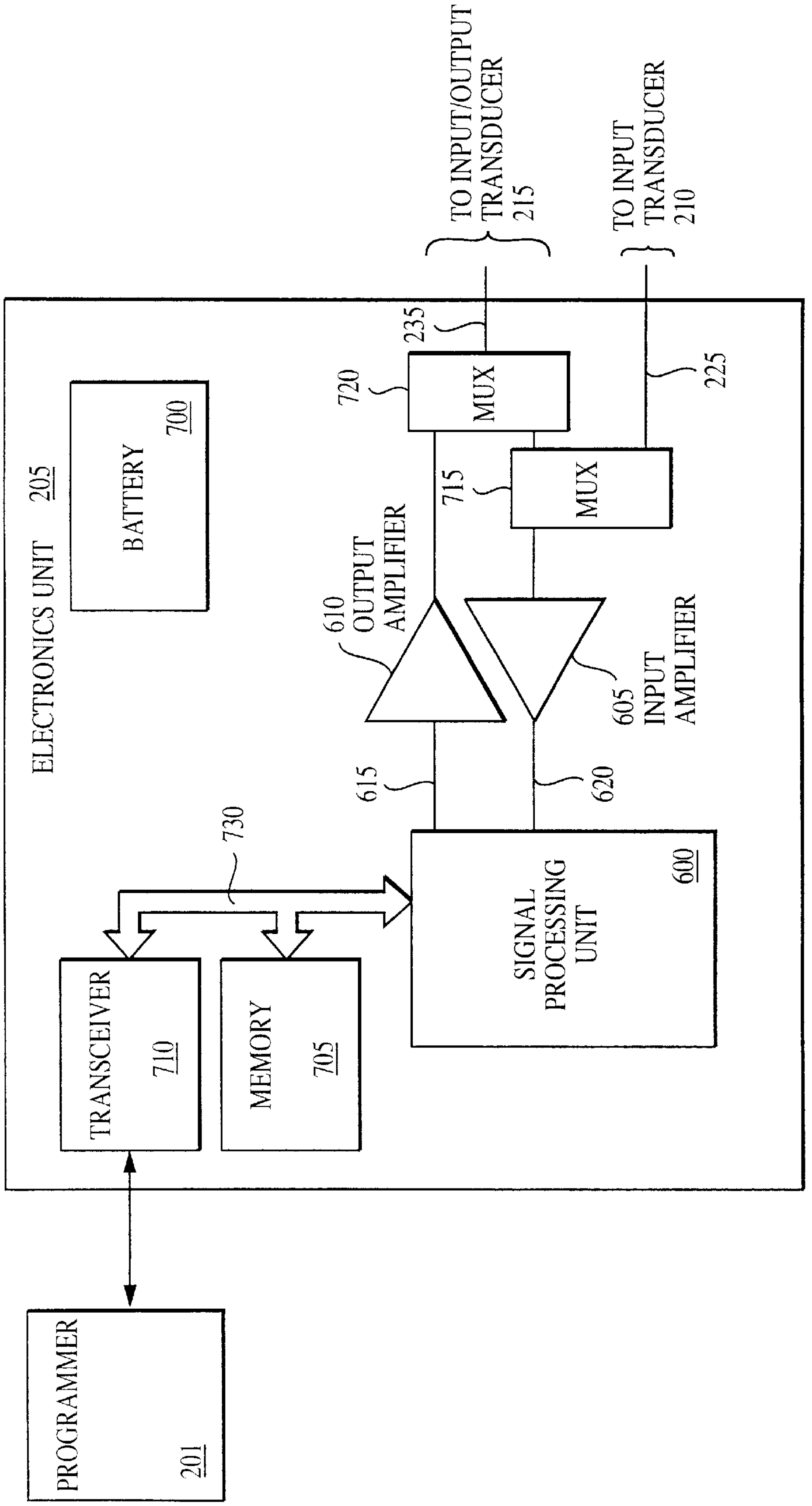
FIG. 7 is a schematic/block diagram illustrating generally a further embodiment of at least a portion of an electronics unit according to another aspect of the present invention.

FIG. 7 is a schematic/block diagram illustrating generally, by way of example, but not by way of limitation, a further embodiment of at least a portion of electronics unit 205 according to one embodiment of the present invention. In the embodiment of FIG. 7, electronics unit 205 also includes battery 700, memory 705, a transmitter such as transceiver 710, and analog multiplexers 715 and 720. FIG. 7 also illustrates external programmer 201, included in one embodiment of the hearing assistance system of the present invention, which includes a receiver or transceiver that is adapted to be communicatively coupled to electronics unit 205, as described above. Battery 700 provides power to the various electrical components of electronics unit 205.

In one embodiment, analog multiplexer 720 allows the electrical output signal provided by output amplifier 610, and the electrical input signal resulting from the evoked otovibratory response to share common lead wires at node 235 for electrical coupling to input/output transducer 215. In another embodiment, multiplexer 720 is omitted, and separate lead wires are provided, illustrated generally by node 235, for separately communicating the electrical output signal from output amplifier 610 and the electrical input signal from input/output transducer 215. In yet another embodiment, in which otovibratory or otoacoustic emissions are sensed via input transducer 210, rather than sensing otovibratory emissions through input/output transducer 215, analog multiplexers 715 and 720 are omitted.

In one embodiment, analog multiplexer 715 allows shared use (e.g., time multiplexed) of input amplifier 605 for amplification of both the input electrical signal provided by input transducer 210 (during hearing assistance mode) as well as the input electrical signal provided by input/output transducer 215 in response to the a evoked otovibratory emission from cochlea 60 (during diagnostic mode). In another embodiment, analog multiplexer 715 is omitted, and input amplifier 605 is separately implemented as two input amplifiers for respectively amplifying the input electrical signal provided by input transducer 210 and the input electrical signal provided by input/output transducer 215 in response to the evoked otovibratory emission from cochlea 60.

In one embodiment, signal processing unit 600 includes circuits for filtering and other signal processing, analog-to-digital conversion, and a microprocessor or other microcontroller. In this embodiment, signal processing unit 600 is electrically coupled to memory 705 and transceiver 710, such as by bus 730. In one embodiment,memory 705 is integrally formed on a monolithic integrated circuit together with signal processing unit 600. Memory 705 is capable of storing data, such as data based on the electrical input signal received from input/output transducer 215 in response to sensed evoked otovibratory or otoacoustic emissions from cochlea 60, or data based on the electrical input signal received from input transducer 210 (e.g., piezoelectric bimorph or microphone) in response to sensed evoked otovibratory or otoacoustic emissions from cochlea 60. Transceiver 710 is capable of transmitting to external programmer 201, or other external transceiver, data based on sensed evoked otovibratory or otoacoustic emissions from cochlea 60.

In one embodiment, transceiver 710 is also capable of receiving data from programmer 201 and communicating the received data to memory 705 for storage or to signal processing unit 600.

According to one aspect of the present invention, the detection of otovibratory or otoacoustic emissions from cochlea 60 is used as a clinical diagnostic tool during surgical implantation of portions of hearing assistance device 200. In one embodiment, input/output transducer 215 (or output transducer 215B) is positioned by the implanting physician for directly or indirectly stimulating cochlea 60 in response to environmental sounds sensed by input transducer 210. In this embodiment, the presence of otovibratory or otoacoustic emissions can indicate proper positioning of input/output transducer 215 (or output transducer 215B).

Figure 8:
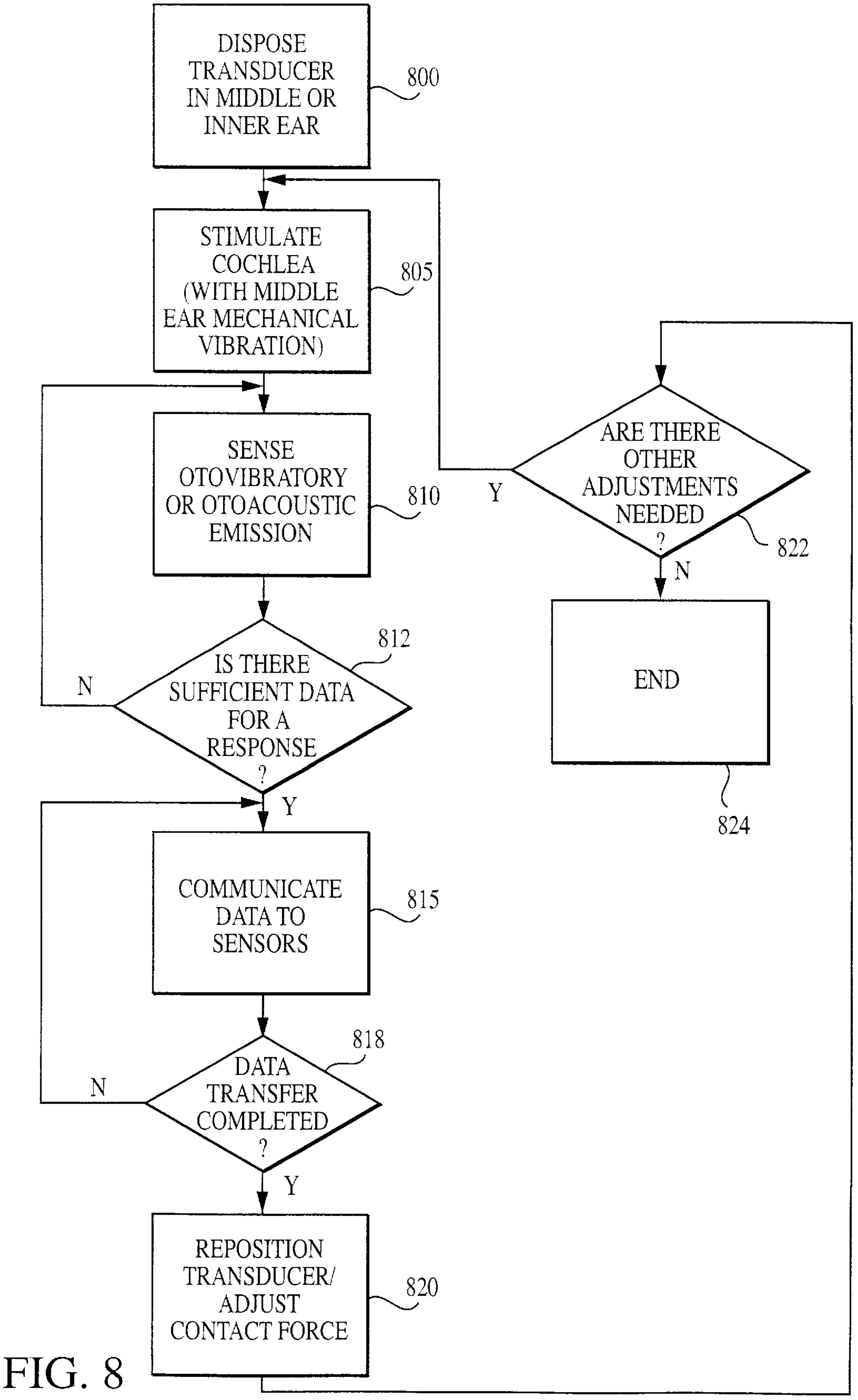
FIG. 8 is a flow chart illustrating generally one embodiment of a method of using the present invention for providing diagnostic information during implantation of portions of a hearing assistance device.

FIG. 8 is a flow chart illustrating generally one embodiment of a method of using the present invention for providing diagnostic information during implantation of portions of hearing assistance device 200. First, an access hole 85 is created, as described above, for disposing components of hearing assistance device 200 in middle ear 35. At logic step 800, a transducer, such as input/output transducer 215, is disposed in middle ear 35. The transducer is communicatively coupled to electronics unit 205. In one embodiment, for example, input/output transducer 215 is electrically coupled to electronics unit 205, such as through one or more lead wires at node 235.

At logic step 805, cochlea 60 is directly or indirectly stimulated. In one embodiment, input/output transducer 215 (or output transducer 215B) provides a mechanical vibration stimulus in middle ear 35 that is coupled to oval window 55 of cochlea 60 through stapes 50.

At logic step 810, an otovibratory or otoacoustic emission, evoked in response to the stimulus of logic step 805, is sensed by input/output transducer 215 or input transducer 210. The resulting electrical input signal is converted into a digital data signal, such as by an analog-to-digital (A/D) converter included in signal processing unit 600. Subsequently, the program logic checks to see if there is sufficient data for a response under decision step 812. If the response to the query is in the affirmative, the program logic proceeds to logic step 815. In the alternate, if the response is negative, the program logic reverts into a subroutine and goes back to logic step 810. After the program logic proceeds to logic step 815 data signal based on the sensed otovibratory or otoacoustic emissions is communicated at logic step 815 from an implanted transmitter, such as transceiver 710, to an external receiver, such as within programmer 201. Subsequently, the program logic checks to see if data transfer is completed under decision block 818. If the data is completed the program logic proceeds to logic step 820 where the transducer is repositioned or the contact force adjusted. In the alternate, if the data transfer is not completed, the program logic enters a subroutine and reverts back to logic step 815. After logic step 820, the program logic proceeds to decision block 822 where the need for further adjustments, if any, is checked. In the event there is such a need, the program logic goes into a subroutine and reverts back to logic step 805. In the alternate, if no other adjustments are required, the program logic advances to logic step 824 and the operation is completed.

The data received by programmer 201 is displayed for the implanting physician on any type of display device, including but not limited to a screen display or a quartz readout. The displayed data allows the implanting physician to determine the amplitude of any detected otovibratory or otoacoustic emissions. If no otovibratory or otoacoustic emission is sensed, or inadequate amplitude is obtained, the implanting physician optionally reposition the transducer (e.g., input/output transducer 215 or output transducer 215B) at logic step 820. Logic steps 805 through 820 are optionally repeated until an adequate otovibratory or otoacoustic emission signal is obtained. In other words, the detection of otovibratory or otoacoustic emissions is used as a feedback signal to enable the physician to correctly position the implant so that adequate signals will be produced. In one embodiment, otovibratory or otoacoustic responses resulting from several stimulations of cochlea 60 are averaged to provide the resulting data signal communicated from transceiver 710.

Thus, according to one aspect of the invention, otovibratory or otoacoustic emissions are used to provide diagnostic information to assist the implanting physician in positioning components of a hearing assistance device 200, such as an electrical-to-mechanical output transducer in a P-MEI or T-MEI hearing assistance device.

According to another aspect of the invention, otovibratory or otoacoustic emissions are used to provide diagnostic information to optimize a force between input/output transducer 215 (or output transducer 215B) and a corresponding auditory element that it contacts (e.g., stapes 50). In one embodiment, for example, the contact force is selected based on the desired output vibration frequency. In yet another embodiment, for example, multiple output transducers, each having a different frequency response, optimize an overall frequency response of vibrations delivered to cochlea 60, as described in a co-pending U.S. patent application to Kroll et al. entitled IMPLANTABLE HEARING SYSTEM HAVING MULTIPLE TRANSDUCERS, Ser. No. 08/693,430, filed on Aug. 7, 1996, and assigned to the assignee of the present application, and which is herein incorporated by reference.

According to one aspect of the present invention, a vibration is provided, at logic step 805, within (e.g., near the center of the passband) the particular output transducer's frequency range. The contact force between the output transducer and its corresponding auditory element (e.g., stapes 50) is adjusted at logic step 820 to maximize the amplitude of the resulting otovibratory or otoacoustic emission sensed at step 810. In one example, a tighter connection is provided for an output transducer vibrating at higher frequencies (e.g., frequencies that are greater than 1 kHz) and a looser connection is provided for a different output transducer vibrating at lower frequencies (e.g., frequencies that are lower than 1 kHz).

According to another aspect of the invention, otovibratory or otoacoustic emissions are used to noninvasively provide diagnostic information in a newly or chronically implanted hearing assistance device, for example hearing assistance device 200. By executing logic steps 805, 810, and 815 on an already-implanted hearing assistance device 200, the physician can determine whether input/output transducer 215 (or output transducer 215B) remains in proper contact with a corresponding auditory element (e.g., stapes 50) for directly or indirectly vibrating cochlea 60.

In one embodiment, for example, a piezoelectric bimorph input/output transducer 215 is mounted such that it contacts stapes 60 for delivering mechanical vibrations to cochlea 60 through stapes 50. However, input/output transducer 215 may become dissociated from stapes 50 (e.g., by a severe blow to the patient's head or otherwise). Also, fibrous ingrowth may change the interface characteristics (such as interfacial force) between input/output transducer 215 and stapes 50. If otovibratory or otoacoustic emissions were present immediately after hearing assistance device 200 was implanted, data communication indicating the absence of such otovibratory or otoacoustic emissions at a subsequent follow-up patient examination may noninvasively indicate inadequate stimulation by input/output transducer 215.

In another embodiment, the otovibratory or otoacoustic emission data communicated by hearing assistance device 200 to programmer 201 is used in conjunction with other auditory response testing techniques, including, but not limited to: electric response audiometry (ERA), auditory brain-stem response (ABR), cortical electric response, electrocochleography, or other known audiometric techniques. Examples of auditory response testing techniques are described in a copending U.S. patent application to Kroll et al. entitled IMPLANTABLE HEARING ASSISTANCE SYSTEM WITH CALIBRATION AND AUDITORY RESPONSE TESTING, Ser. No. 08/804,016, filed on Feb. 21, 1997, and assigned to the assignee of the present application, and which is herein incorporated by reference. One aspect of the present invention allows the physician to differentiate between cochlear and neural problems. For example, if hearing assistance device 200 indicates the presence of otovibratory or otoacoustic emissions, but accompanying ABR tests fail to obtain a response signal, the origin of the hearing disfunction is likely neural, not cochlear.

Figure 9:
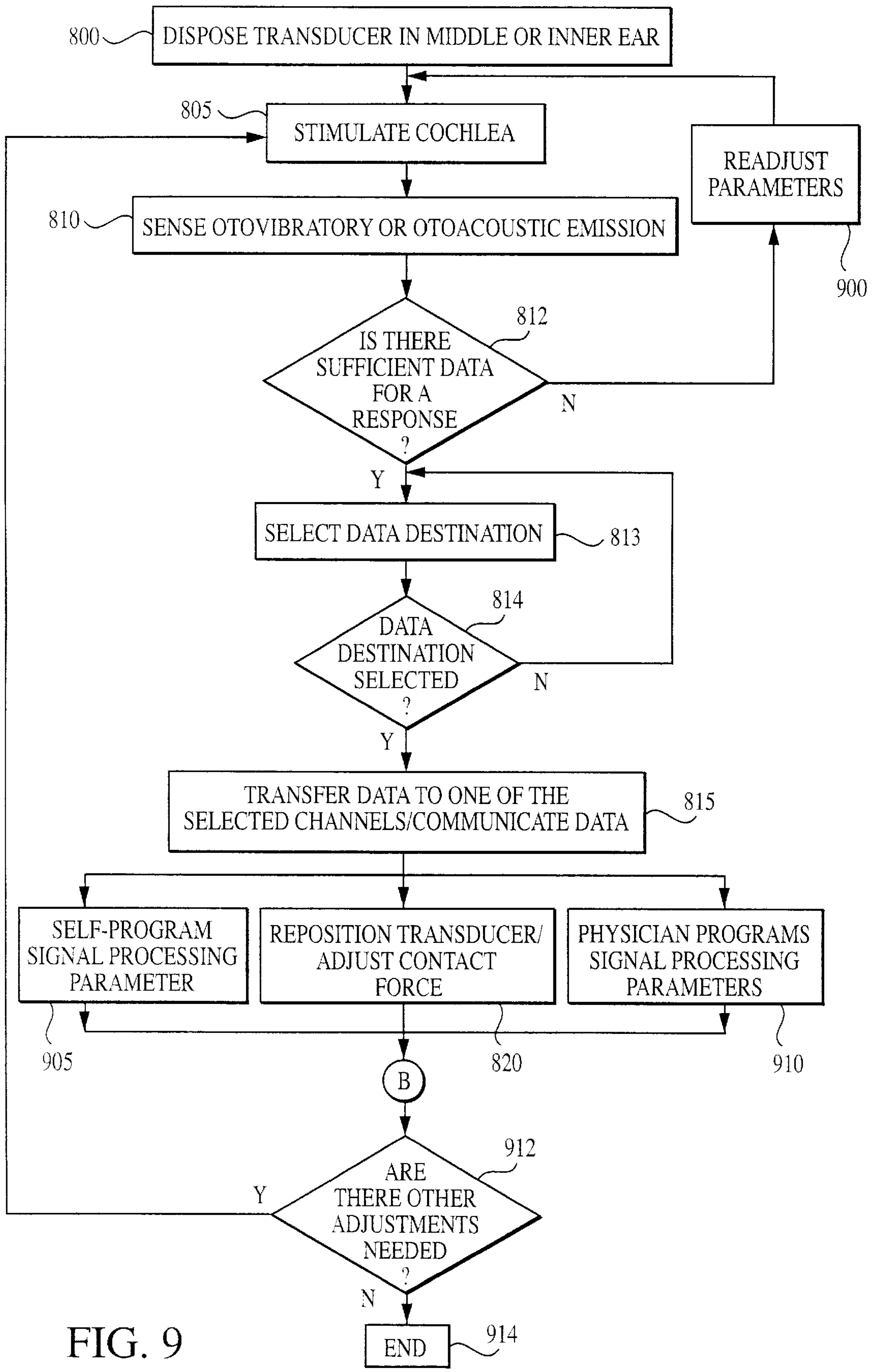
FIG. 9 is a flow chart illustrating generally a further embodiment of a method of using the present invention.

FIG. 9 is a flow chart, similar to FIG. 8, illustrating generally a further embodiment of a method of using the present invention in which signal processing unit 600 provides an automated sequence of stimulation logic step 805 and otovibratory or otoacoustic sensing logic step 810. The method of FIG. 9 further provides intermediate parameter readjustment at logic step 900, as described below. Parameter adjustment at step logic step 900 includes, but is not limited to, adjustment of vibrational stimulation amplitude and frequency.

In one embodiment, for example, tone burst vibrational stimulations are provided at 500 Hz, 1 kHz, 2 kHz, 4 kHz, followed by a wideband click (e.g., containing frequency content substantially throughout the range between 500 Hz and 4 kHz). At each such frequency content setting, the amplitude of the vibrational stimulation may also be varied, such as by incrementally increasing the amplitude of the vibrational stimulation from 40 dB SPL to 100 dB SPL at 20 dB SPL increments. These frequencies and amplitudes are enumerated above by way of example only, and not by way of limitation. Other sequences of the frequency and amplitude of the vibrational stimulation may also be used.

In another embodiment, for example, where the patient's degree of hearing loss is already known, such information is provided to hearing assistance device 200 by the physician via programmer 201, and the parameter readjustment at logic step 900 is tailored accordingly. For example, but not by way of limitation, for a patient having a hearing loss of approximately 40 dB at frequencies less than 1 kHz, and a hearing loss of approximately 60 dB at frequencies greater than 1 kHz, vibrational stimuli are sequentially delivered according to Table 1. For other patients having different hearing losses, frequencies and amplitudes different from those in Table 1 are used.

TABLE 1

Patient with 40 dB loss < I kHz and 60 dB loss > I kHz

| Frequency (Hz) | Amplitude (dB SPL at stapes) |
|---|---|
| 500 | 40, 60, 80, 100 |
| 1000 | 40, 60, 80, 100 |
| 2000 | 60, 80, 100 |
| 4000 | 60, 80, 100 |
| Wideband (e.g., 500 Hz–4000 Hz) | 40, 60, 80, 100 |

After the automated sequence of stimulation logic steps 805, otovibratory or otoacoustic sensing logic steps 810, and parameter readjustment logic steps 900, the data is optionally communicated to the physician at logic step 815. In one embodiment, such as during implantation of portions of hearing assistance device 200, the physician then repositions input/output transducer 215 or adjusts the contact force at logic step 820. Signal processing unit 600 is capable of adjusting an electrical output signal to input/output transducer 215, such as based on the received electrical first input signal from input/output transducer 215. In one embodiment, signal processing unit 600 self-programs hearing assistance device 200, adjusting certain hearing assistance signal processing parameters (e.g., gain, frequency response, noise filtering) at step 905, based on the otovibratory or otoacoustic emission data sensed at step 810. Alternatively, the physician intervenes and manually programs such hearing assistance signal processing parameters at step 910 based on the data communicated at step 815. Thus, programming the hearing assistance device 200 can be either with or without physician intervention. Looking at FIG. 9 in more detail, The program is initiated under logic step 800 by disposing the transducer in the middle ear. Consequently, the cochlea is stimulated under logic step 805. The program logic proceeds to logic step 810 where the vibrations (otovibratory or otoacoustic emission) are sensed. Under the subsequent decision block 812, the program logic checks to verify if there is sufficient data for a response. In the vent it is found that the data is not sufficient the program logic goes into a subroutine and reverts back to logic step 805. In the alternate, if the data is found to be sufficient, the program logic proceeds to logic step 813 where the data destination is set or selected. Decision block 814 confirms the selection of data destination. If no selections are available, the program logic goes into a subroutine and reverts back to logic step 813. In the event that at least one data destination is selected, the program logic proceeds to logic step 815 where data transfer to one of the selected channels is executed. Accordingly, data may be transferred to modify signal processing parameters under logic step 905, reposition transducer/ adjust contact force under logic step 820 and enable the physician to program signal processing parameters under logic step 910. Subsequently, the program logic proceeds to decision block 912 to check if there is a need for other adjustments. In the event there is a need to modify or make adjustments, the program logic enters a subroutine and reverts back to logic step 805. In the alternate, if no other adjustments are needed or indicated, the program logic proceeds to logic step 914 where the session is terminated.

Accordingly, the present invention provides a transient middle ear mechanical vibration stimulus, and senses an evoked otovibratory or otoacoustic emission from the cochlea. Based on the sensed emissions, diagnostic information is provided to the physician, allowing easier positioning and coupling of an electrical-to-mechanical output transducer. In other words, the detection of otovibratory or otoacoustic emissions is used as a feedback signal to enable the physician to correctly position the implant so that adequate signals will be produced. Diagnosis of auditory system or hearing assistance system malfunctions is easier using the data communicated from the implantable hearing assistance device. Signal processing parameters are adjusted based on the sensed cochlear emissions. Cochlear emissions are also more likely to be detected with improved sensitivity.

It is to be understood that the above description is intended to be illustrative, and not restrictive. Combinations of the above-described embodiments are also included within the scope of the present invention. Many other embodiments will be apparent to those of skill in the art upon reviewing the above description. The scope of the invention should, therefore, be determined with reference to the appended claims, along with the full scope of equivalents to which such claims are entitled.

What is claimed is:

1. In a hearing device, a method for detecting cochlear emissions and performing audiometric, calibration and diagnostic functions in at least partially implantable hearing assistance system wherein an optimal orientation and affixation of the hearing assistance system is ensured, the device-implemented steps comprising:

installing a transducer adapted for sensing mechanical vibrations produced by an inner ear;

sensing one of transient evoked otovibratory and otoacoustic emissions from the inner ear;

generating a signal in response to the emission; and programming the hearing device based on said signal.

2. The method according to claim 1 wherein said transducer includes an output and input transducers.

3. The method according to claim 2 wherein said output transducer is adapted for coupling a mechanical vibration output stimulus device directed to the inner ear responsive to an electrical output signal.

4. The method according to claim 2 wherein said input transducer is adapted for receiving one of said transient evoked otovibratory and otoacoustic emissions from the inner ear and generating an electrical first input signal in response to the emissions.

5. The method according to claim 1 further including the step of adjusting the signal based on an input signal.

6. The method according to claim 1 further including the device-implemented steps of:

stimulating the inner ear using the transducer disposed in the middle ear; and sensing said emissions from the inner ear.

7. The method according to claim 1 further including the step of adjusting a stimulation of the inner ear based on the sensed emissions from the inner ear.

8. The method according to claim 1 further including the step of storing at least one data signal based on emissions from the inner ear.

9. The method according to claim 8 wherein said signal is based on a communication data between a transmitter implanted in the ear and an external receiver.

10. The method according to claim 1 wherein said step of programming includes repositioning the transducer based on the sensed emission from the inner ear.

11. The method according to claim 10 wherein said step of repositioning includes adjusting a contact force between the transducer and an auditory element based on the sensed emission from the inner ear.

12. The method according to claim 1 further including the device-implemented steps of:

stimulating the inner ear;

sensing emissions from the inner ear in response to said step of stimulating; and programming the device by adjusting one of gain and frequency response based on the sensed emissions in the inner ear.

13. A hearing assistance system including components for detecting transient evoked cochlear emissions including mechanical sound vibrations and resultant sound pressure waves wherein the detection of the emissions enables signal generation for calibration and diagnostic functions, the hearing assistance systems and the components in combination, comprising:

an electronic unit;

an input transducer;

an integrated input and output transducer; and a programmer; said electronics unit being in operable electrical contact with said input transducer, said input and output transducer and said programmer.

14. The system of claim 13 wherein said electronics unit is adapted to be implantable in a human ear.

15. The system of claim 13 wherein said electronics unit is implantable in at least one of pectoral, dorsal, cranial and subcranial locations.

16. The system of claim 13 wherein said programmer is structured to being in wireless communication with said hearing assistance system.

17. The system of claim 16 wherein said hearing assistance system includes one of at least a receiver and a transmitter combination and a transceiver.

18. A device adapted for sensing mechanical vibrations produced by an inner ear wherein the mechanical vibrations include transient evoked otovibratory and evoked otoacoustic emissions, the device being integrated with a hearing assistance system, the device comprising:

an output transducer adapted for generating mechanical vibrations output stimulus to the inner ear in response to an electrical output signal; and a first transducer adapted for receiving the emissions from the inner ear and generating an electrical first input signal in response to the emissions.

19. The device of claim 18 wherein the output and first input transducers are integrated to form a unit.

20. The device of claim 18 wherein the output and first input transducer are separately formed.

21. The device of claim 18 wherein the output transducer is an electromechanical transducer of one of piezoelectric and electromagnetic type.

22. The device of claim 18 wherein the first input transducer is one of piezoelectric, electromagnetic, capacitive, accelerometers and microphones.

23. The device of claim 18 wherein the first input transducer is adapted to receive ambient/environmental sounds.

24. The device of claim 18 wherein the first input transducer is adapted to provide a mechanical vibration for coupling to the inner ear.

25. The device of claim 18, further comprising an electronics unit, electrically coupled to the output transducer for providing the electrical output signal, wherein the electronics unit is capable of adjusting the electrical output signal based on the received electrical first input signal.

26. The device of claim 18, further comprising an electronics unit, electrically coupled to the first input transducer for receiving the electrical first input signal and also electrically coupled to the output transducer for providing the electrical output signal wherein the electronics unit is capable of adjusting the electrical output signal based on the received electrical first input signal.

* * * * *